United States Patent
Eikman et al.

(10) Patent No.: US 9,138,235 B2
(45) Date of Patent: Sep. 22, 2015

(54) DISPOSABLE VENOUS TOURNIQUETS AND METHODS OF USE

(75) Inventors: Edward A. Eikman, Tampa, FL (US); Adam D. Eikman, Tampa, FL (US); E. Allan Eikman, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 134 days.

(21) Appl. No.: 13/995,598

(22) PCT Filed: Dec. 20, 2011

(86) PCT No.: PCT/US2011/066010
§ 371 (c)(1),
(2), (4) Date: Jun. 19, 2013

(87) PCT Pub. No.: WO2012/088027
PCT Pub. Date: Jun. 28, 2012

(65) Prior Publication Data
US 2013/0304113 A1    Nov. 14, 2013

Related U.S. Application Data

(60) Provisional application No. 61/459,890, filed on Dec. 21, 2010, provisional application No. 61/463,255, filed on Feb. 15, 2011, provisional application No. 61/463,423, filed on Feb. 17, 2011.

(51) Int. Cl.
| | | |
|---|---|---|
| *A61B 17/132* | (2006.01) | |
| *A61B 17/08* | (2006.01) | |
| *A61B 19/02* | (2006.01) | |
| *A61B 17/00* | (2006.01) | |
| *A61B 19/00* | (2006.01) | |

(52) U.S. Cl.
CPC ......... *A61B 17/1327* (2013.01); *A61B 17/1322* (2013.01); *A61B 17/085* (2013.01); *A61B 19/026* (2013.01); *A61B 2017/00084* (2013.01); *A61B 2017/00951* (2013.01);
(Continued)

(58) Field of Classification Search
CPC ...... A61B 17/00; A61B 17/12; A61B 17/132; A61B 17/1325; A61F 13/02
USPC ........ 606/201–203; 24/163 R, 300, 301, 304, 24/306, 448, 451, 16 PB
See application file for complete search history.

(56) References Cited

U.S. PATENT DOCUMENTS

| | | | | |
|---|---|---|---|---|
| 4,243,039 A | * | 1/1981 | Aginsky | 606/203 |
| 5,133,671 A | * | 7/1992 | Boghosian | 439/371 |

(Continued)

OTHER PUBLICATIONS

International Search Report for PCT/US2011/066010.

*Primary Examiner* — Todd Manahan
*Assistant Examiner* — Casey B Lewis
(74) *Attorney, Agent, or Firm* — Caesar Rivise, PC

(57) ABSTRACT

A disposable tourniquet and its method of use is disclosed. The tourniquet is in the form of a band formed of a thin flexible, non-stretchable material and has releasable securable means, e.g., a pressure sensitive adhesive. The tourniquet is arranged to be wrapped around the patient's limb, tightened and locked in place to reduce circulation. The tourniquet has means for controlling the amount of tension applied to the band when it is tightened about the limb of the patient, means for indicating the amount of tension applied. Means for indicating the ambient temperature at the patient's limb on which the tourniquet is used may be included in the tourniquet. The tourniquet may also include means to enable it to be folded into a compact configuration. Plural tourniquets can be provided in the form of a stack.

20 Claims, 4 Drawing Sheets

(52) U.S. Cl.
   CPC .. *A61B 2019/0219* (2013.01); *A61B 2019/461* (2013.01); *A61B 2019/464* (2013.01)

(56) References Cited

U.S. PATENT DOCUMENTS

| | | | | |
|---|---|---|---|---|
| 5,219,356 A | * | 6/1993 | Harreld et al. | 606/203 |
| 6,129,964 A | * | 10/2000 | Seth | 428/40.1 |
| 6,149,618 A | * | 11/2000 | Sato | 602/75 |
| 6,152,893 A | * | 11/2000 | Pigg et al. | 602/75 |
| 2005/0049630 A1 | | 3/2005 | Ambach | |
| 2007/0250109 A1 | * | 10/2007 | Kerstein et al. | 606/203 |
| 2008/0077205 A1 | * | 3/2008 | Cazzini | 607/104 |
| 2008/0262534 A1 | * | 10/2008 | O'Neil | 606/203 |
| 2009/0062843 A1 | * | 3/2009 | Heston | 606/203 |
| 2011/0137336 A1 | * | 6/2011 | Holcomb et al. | 606/203 |

* cited by examiner

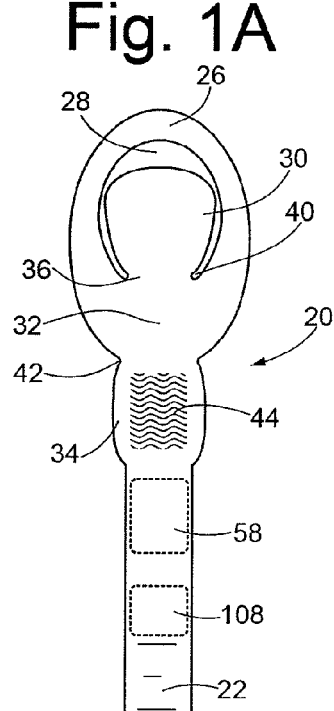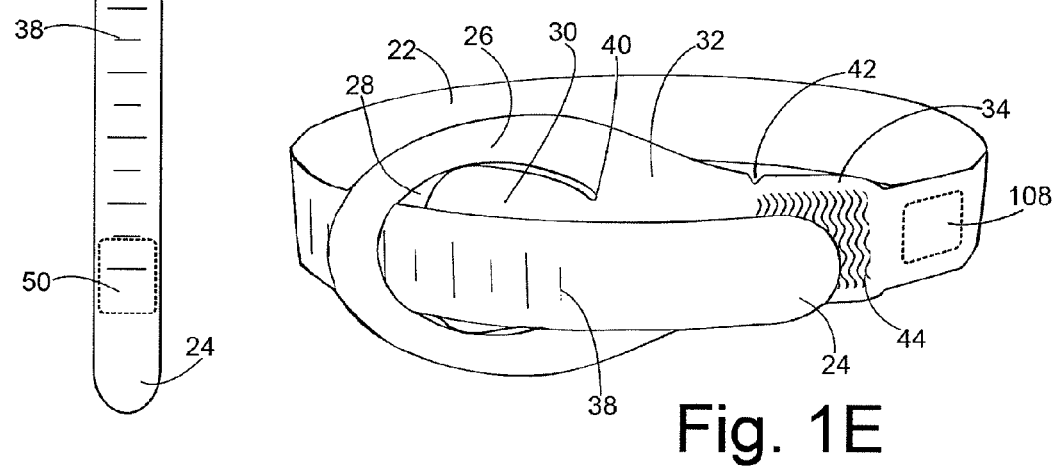

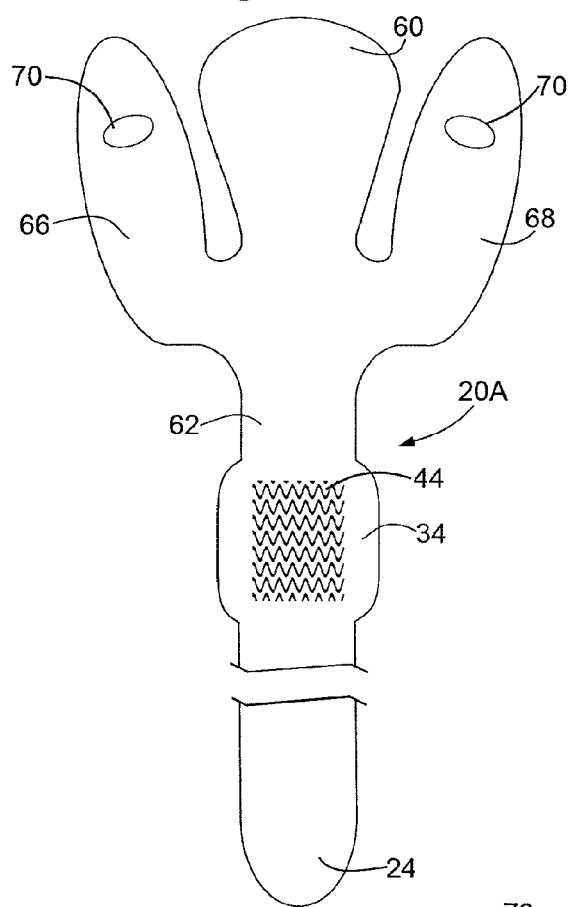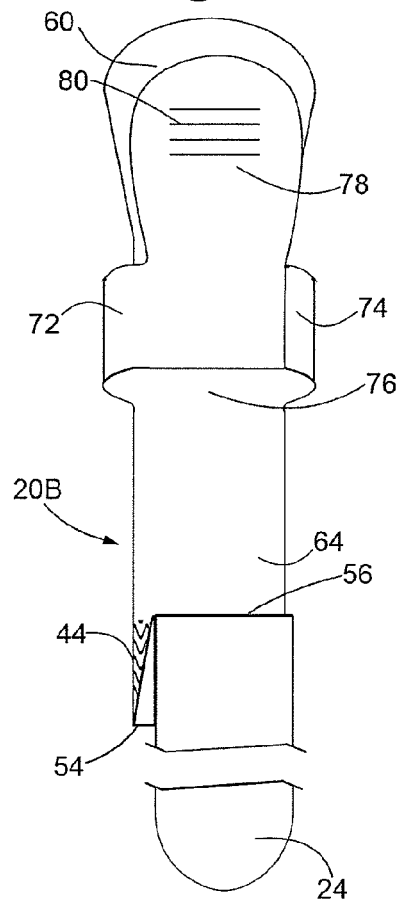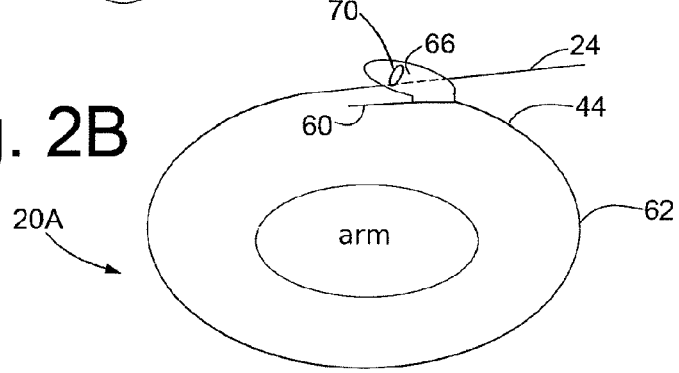

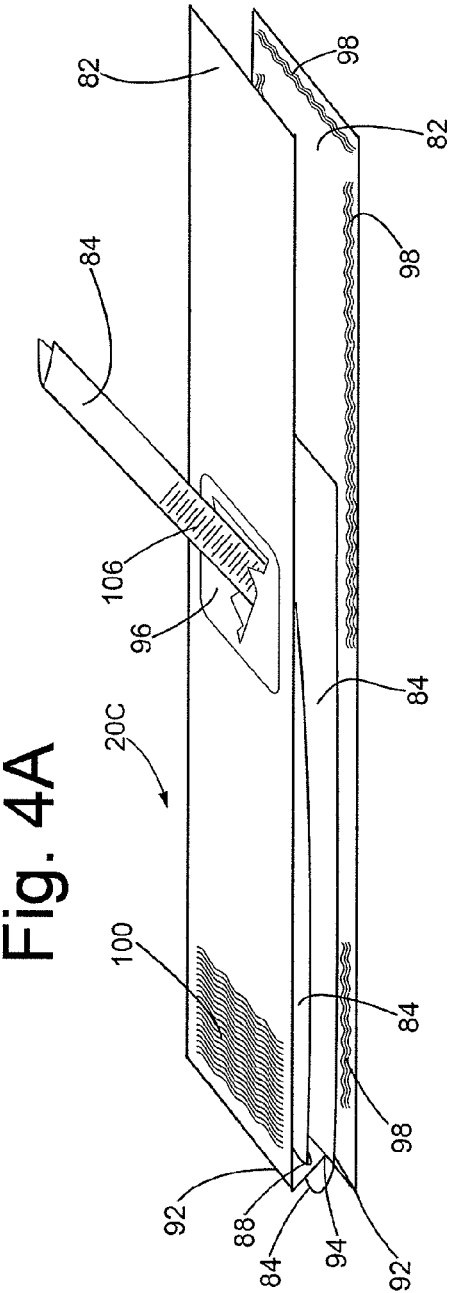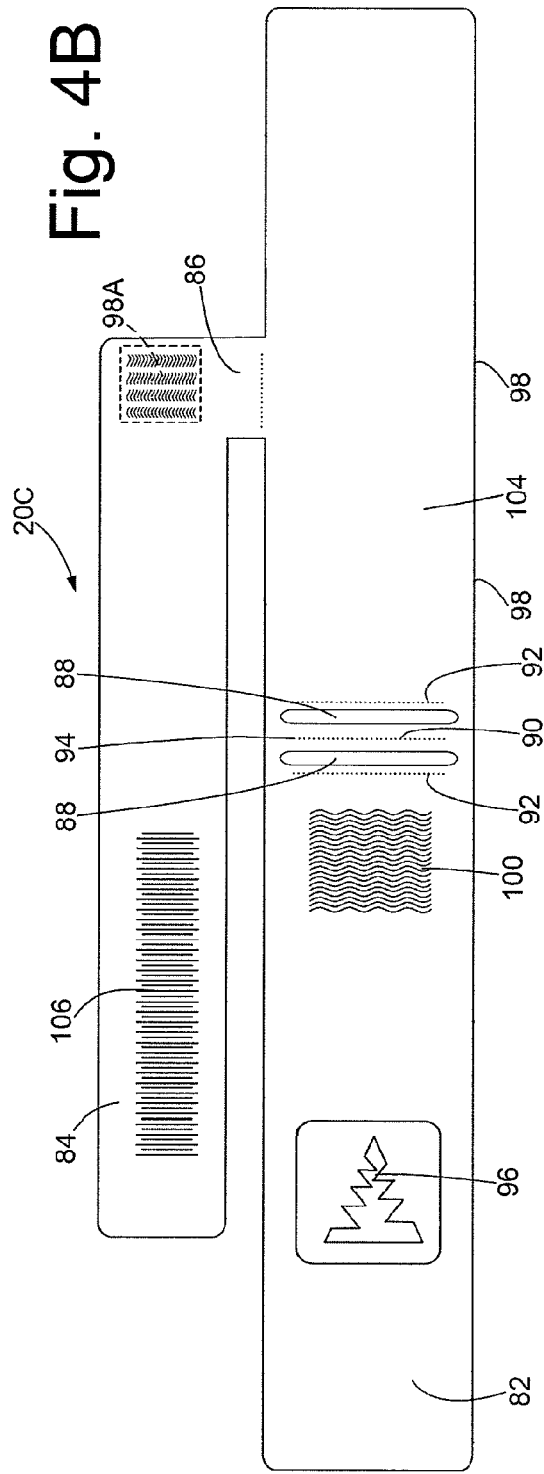

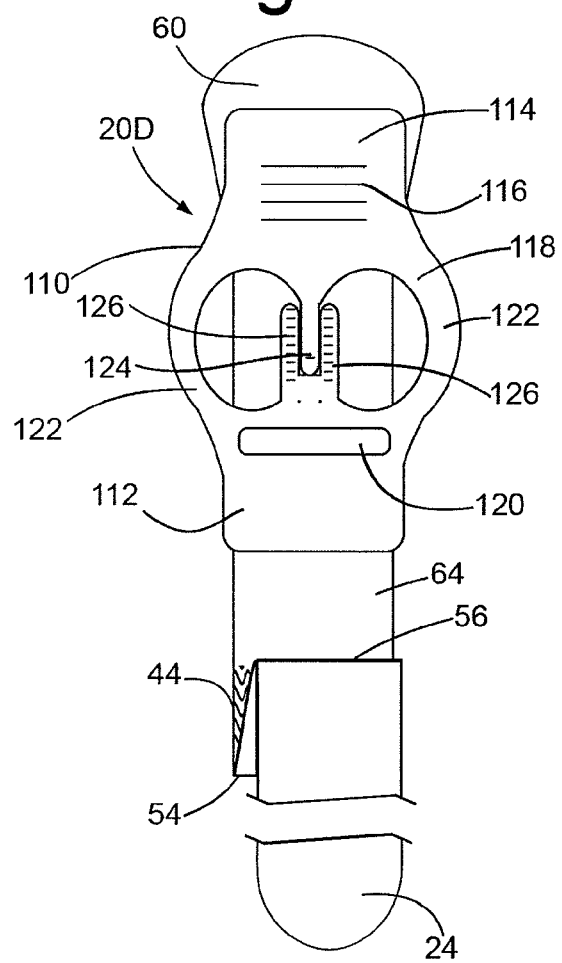

DISPOSABLE VENOUS TOURNIQUETS AND METHODS OF USE

CROSS REFERENCE TO RELATED APPLICATIONS

This application claims the benefit of Provisional Patent Application Ser. No. 61/459,890 filed on Dec. 21, 2010, entitled Venous Tourniquet And Method Of Use, Provisional Patent Application Ser. No. 61/463,255, filed on Feb. 15, 2011, entitled Disposable Venous Tourniquet And Method Of Use, and Provisional Patent Application Ser. No. 61/463,423 filed on Feb. 17, 2011, entitled Disposable Venous Tourniquet And Method Of Use, all of whose disclosures are incorporated by reference herein.

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

BACKGROUND OF THE INVENTION

1. Field of the Invention

This invention relates to generally to medical devices and more particularly to tourniquets, e.g., venous tourniquets which are used during a venipuncture process of withdrawing blood from a limb of a patient, and methods of using the same.

2. Prior Art

The process of venipuncture is eased by the use of a tourniquet to increase tissue pressure to retard venous flow, thereby to facilitate the distention of veins along an extremity such as an arm or leg. By applying a venous tourniquet the vein enlarges, becomes more visible, and the wall is tensioned, helping to facilitate needle entry in the proper location and depth with less prolonged patient discomfort. The tissue pressure achieved is ideally just sufficient to accomplish distension with minimal discomfort, and without interference in arterial flow. Less tissue pressure may be required if the patient is not subject to peripheral venous vasoconstriction, as when the care environment is cool, and venous vasoconstriction influences strive to retain body heat.

A rubber strip is most commonly used as a low cost venous tourniquet, by stretching, then releasing a locked length of strip to apply pressure to the tissue. As the tourniquet is looped and tightened around the extremity, the elastic material narrows and buckles inward as pressure along the arm is focused on less surface area. This property of rubber prevents the tourniquet from realizing the spread profile of pressure which is both effective and comfortable. It is also difficult to estimate the actual pressure being applied when the stretched rubber is released to apply to the extremity. The rubber strip tourniquet is commonly secured with a tuck hitch which may slip and snap back, and uses a variable, uncertain length of strip, further impairing estimation of the actual tissue pressure being applied. Upon securing the tourniquet, the patient often feels a pinching sensation located where the band intersects itself, or due to narrowing of the band with tightening. In addition, the application of the tourniquet typically may move the extremity as the tourniquet is pulled away from the extremity and with over tightening in order to gain enough slack to secure a tuck hitch. Then as the process is finished, the patient may experience additional pinching and hair pull as the skin is stretched along the extremity, and at the tuck. With application of the tourniquet complete, the person applying the tourniquet does not have a direct way of feeling or otherwise appreciating the tension of the tourniquet, no more than necessary to achieve distension. Even experienced users may not consistently provide the appropriate amount of tension. Although under-tension is evident because or poor venous distension, a user may consistently over tension the tourniquet failing to learn to adjust tension appropriately.

Several improvements over the rubber strip have been disclosed in the patent literature. For example, U.S. Pat. No. 3,930,506 (Overand) discloses a disposable tourniquet with an adhesive strip protected by a liner. The feature eliminates the need to tie a tuck hitch, but the release liner has to be removed producing waste material. Moreover, the device is elastic so that it becomes narrower and buckles inward as tension increases. Further still, it has no means to indicate the level of tension.

U.S. Pat. No. 5,219,356 (Harreld) discloses a device which addresses the problem of producing additional waste material by folding over a portion of the tourniquet with the release liner attached. Like the Overand device, the device of Harreld is made with an elastic material and has no tension indication. In addition, the device has no grip for a user's second hand to hold during application, such that the second end of the tourniquet must pass over and rest on top of the fingers (holding the first end in place) before contacting the pressure sensitive adhesive. When the fingers are removed the tension changes unpredictably.

U.S. Published Patent Publication 2007/0250109 (Kerstein et al.) discloses a tourniquet which attempts to solve that problem by introducing a grip region and an aperture or though hole for the other end. However, the feature of Kerstein et al. for achieving that end leads to a several problems. In particular, as the tourniquet is tightened the aperture becomes a pinch point and skin will push though the location. In addition, like the other devices described above the device of Kerstein et al. has no tension indication.

U.S. Pat. No. 5,540,714 (Lundberg et al.) is directed to a disposable tourniquet which prevents slippage making it easier to knot and results in less pulling of skin and hair, but the tourniquet's band still narrows as tension is increased. Moreover, as is the case of the other prior art described above, the device of Lundberg et al. doesn't provide any tension indication.

Several patents do, however, disclose tension indication, e.g., U.S. Pat. No. 3,613,679 (Bijou), U.S. Pat. No. 5,195,950 (Delannoy), U.S. Pat. No. 5,779,659 (Allen) and U.S. Pat. No. 5,894,032 (Green et al.). But these prior art devices all necessitate the use of elastic material as the body of the device in order to function. U.S. Published Patent Application 2009/0062843 (Heston) discloses a device that adds a resilient section to the body of the band. But again elasticity in the body of the device is necessary. U.S. Pat. No 6,149,618 (Sato) provides tension indication by means of a spring which for the purpose of a disposable tourniquet would be cost prohibitive. Comfort features are also described, but the use of the holding ring at the point of intersection between the first and second end of the device would result in skin pushing through the location when tension is applied. A pulley feature is also described, but it lacks a sleeve. Thus, the device cannot slide across the extremity and tissue may be uncomfortably torqued.

U.S. Pat. No. 7,842,067 (Esposito) introduces a sleeve. But there is no direct tension indication other than remembering the number of turns of a rod. Moreover, the features of the Esposito tourniquet constitute a level of complexity which would not be conducive to single use disposable tourniquets.

U.S. Published Patent Application 2008/0177159-A1 (Gavriely) discloses a tourniquet used to stop arterial blood loss that includes a temperature monitor to contribute to diagnostics including to warning signals that usage time is about to expire. There is no provision to indicate ambient temperature to indicate a possible state of peripheral venoconstriction prior to application of a tourniquet to facilitate venipuncture.

To summarize, all of the venous tourniquets described in the prior art suffer from one or more the following disadvantages: pinching of the skin (including where the band intersects itself); pinching and pulling of hair including along the back of the extremity, imprecise or no tension control by the user; use of elastic material which narrows and buckles when stretched, focusing more pressure on less surface; and being cost prohibitive as a disposable tourniquet. Moreover, such devices do not include any ambient temperature feedback to indicate if conditions are ideal for venous distension and typically have excess material which must be removed prior to use or additional behaviors during operation preventing convenient application. Thus, a need presently exists for a low cost, disposable venous tourniquet that enables effective venipuncture with minimal discomfort.

The subject invention addresses that need.

SUMMARY OF THE INVENTION

In accordance with one aspect of this invention there is provided a disposable tourniquet arranged to be wrapped around a patient's limb and tightened to reduce circulation. The tourniquet comprises a band formed of a thin flexible, non-stretchable (inelastic) material. The tourniquet has releasable securable means (e.g., a pressure sensitive adhesive, cooperating hook and loop fastener components, etc.) for enabling it to be wrapped around the patient's limb and tightened. It also includes means (e.g., a tongue and associated components) for preventing pinch and controlling the amount of tension applied to the band when it is tightened about the limb of the patient. If desired the tourniquet may include one or more of the following optional features: means for indicating the amount of tension applied (e.g., indicia on the outer surface of the tourniquet); and means for indicating ambient temperature (e.g., ambient temperature sensitive liquid crystals). If desired, plural tourniquets may be provided in a stack, with each of the tourniquets of the stack being releasably secured to the other tourniquets of the stack.

In accordance with another aspect of this invention there is provided a method of apply a tourniquet constructed like that described above onto the limb of a patient. The method basically entails wrapping the band around the limb of the patient so that a desired amount of tension is applied, whereupon the tourniquet increases tissue pressure to produce venous distention with minimum tissue torsion, and traction to the skin and hair of the patient to prevent pinching of the patient's skin or pulling of the patient's hair.

DESCRIPTION OF THE DRAWING

FIG. 1A is a plan view of one exemplary tourniquet constructed in accordance with the subject invention;

FIG. 1B is a reduced isometric view of a stack of exemplary tourniquets, each of which is constructed like the tourniquet shown in FIG. 1B;

FIG. 1C is a reduced isometric view of the tourniquet of FIG. 1A, but shown being unfolded from a compact folded storage configuration;

FIG. 1D is an isometric view, like that of FIG. 1C but showing the tourniquet being unfolded from an even more compact folded storage configuration;

FIG. 1E is an enlarged isometric view of the tourniquets of FIG. 1A shown in the state where it is ready to be tightened about the limb, e.g., arm, of a patient (the limb not being shown in this figure);

FIG. 2A is a plan view of an alternative exemplary embodiment of a tourniquet constructed in accordance with the subject invention;

FIG. 2B is an illustration taken from a transverse direction showing how the tourniquet of FIG. 2A is disposed about the arm of a patient;

FIG. 3 is an isometric view of an alternative embodiment to the exemplary tourniquet of FIG. 2A, with the alternative embodiment being shown with a plurality of folds provided in the main strip parallel to the main strip and with portions of the tourniquet wrapped around each other;

FIG. 4A is an isometric view of still another alternative exemplary embodiment of a tourniquet constructed in accordance with the subject invention shown in the assembled state where it is ready to be wrapped about the limb, e.g., arm, of a patient (the limb not being shown in this figure);

FIG. 4B is a plan view of the cut sheet of material used to make the tourniquet of FIG. 4A when that sheet is laid flat and ready to be folded and assembled into the tourniquet;

FIG. 5 is an isometric view showing still another exemplary alternative embodiment of the tourniquets of this invention, with the tourniquets of FIG. 5 making use of tab that can be used in place of the tabs of the tourniquets shown in FIGS. 1, 2 and 3.

DETAILED DESCRIPTION OF THE PREFERRED EMBODIMENT

Referring now to the various figures of the drawing wherein like reference characters refer to like parts, there is shown in FIG. 1A one exemplary embodiment of a tourniquet 20 constructed in accordance with this invention.

It must be pointed out at this juncture that the word "exemplary" is used herein to mean "serving as an example, instance, or illustration." Any configuration or design described herein as "exemplary" is not necessarily to be construed as preferred or advantageous over other configurations or designs. Furthermore, use of the words "present invention" or "instant invention" is used herein is meant to include alternative embodiments to the disclosed exemplary embodiments that one of ordinary skill in the art understands. Thus, while some of the embodiments of the invention will be described more fully hereinafter with reference to the accompanying drawings, in which exemplary embodiments are shown, this invention may, however, be embodied in many different forms and should not be construed as limited to the embodiments set forth herein. All statements herein reciting embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Moreover, the functions of the various elements shown in the figures may be provided through the use of materials that may vary in shape, attachment, size, and other physical features.

Thus as can be seen in FIG. 1A the tourniquet basically comprises a band which is preferably cut from a single sheet of flexible, inelastic (non-stretchable) plastic, such as nonwoven olefin fiber or flashspun high density polyethylene such as sold under the trademark TYVEK®. Other suitable non-stretchable materials are also contemplated, such as but not limited to high strength cellulose and composites. The use of an inelastic band which is formed of a relatively smooth material prevents the tourniquet band from narrowing when tension is applied and also prevents the pulling of patient's hair underlying the band. Moreover, the simplicity of the single sheet construction and use of cost effective materials making up the tourniquet promotes economically viable disposal.

The band includes a main strap portion 22 which is of a predetermined and relatively narrow width, e.g., approximately 1 inch (2.54 cm) and terminates in a rounded (e.g., semi-circular) free end 24. A plurality of indicia, e.g., lines, 38 are equidistantly spaced along the strap portion 22. These lines 38 serve as a means to aid the user in determining the amount of tension applied by the tourniquet when it is tightened (as will be described later).

The tourniquet includes a set of features which will be described later which promote comfort, proper and consistent tensioning, and rapid application of the tourniquet. To that end, the opposite end of the strap portion 22 from the free end 24 is in the form of an enlarged tab 26 having a through hole 28 into which a tongue 30 projects. The hole 28 is arranged to receive the free end 24 of the strap portion as shown clearly in FIG. 1E when the tourniquet is placed about the limb of a patient for use. The free end of the strap portion can then be pulled by the user, while the tab portion is pulled or held in place to tighten the tourniquet around the limb, e.g., arm, of the patient.

When the tourniquet has been tightened to the desired level of tension it can be locked into place by releasable securing means. That means is in the form of a pressure sensitive adhesive patch arranged to be releasably secured to the undersurface of the strap portion 22 brought into engagement with it. In accordance with one preferred aspect of this invention the pressure sensitive adhesive patch 44 has approximately 50 oz./in. strength. The patch serves as a locking zone which is arranged to be secured to portion of the underside of the tourniquet's strap portion 22 when the tourniquet is tightened to the desired level of tension. The adhesive patch (locking zone) is preferably surrounded by a blank or clear border area, which serves to keep the patient's hair away from the adhesive. It should be noted that the subject invention contemplates that other releasable locking means, e.g., cooperating multi-hook and multi-loop fastening components (like those sold under the trademark VELCRO®), may be used in lieu of the adhesive patch. Other releasable securing means can be used as well.

As can be seen in FIG. 1E the tongue 30 is wider than the width of the main strap portion 22, such that the tongue flanks the main strap portion 22 when the tourniquet is applied (e.g., wrapped about the arm of the patient). The tab includes a base portion 32 interconnecting it to an intermediate portion 34. The intermediate portion 34 includes the adhesive patch area that forms a locking zone 44 for the tourniquet. The base portion of the tab is wider than the tab itself so as to more evenly distribute tension as the tab is pulled. As the free end 24 of the strap portion 22 is pulled across the tab, the intersection of tension between the tab 26 and the free end 24 is located at the base 32, while the strap portion 22 intersects with the tongue 30. The tongue allows the strap portion 22 to slide until the amount of tension that is on the tourniquet is such that friction shifts the tongue towards the base 32 before the patient's skin underlying the tourniquet is pinched. In particular, as the tongue is shifted forward it begins to crumple into a crumple zone 36, which is located towards the bottom region of the tongue. The crumple zone is the narrower part of the tongue for the purpose of gaining the initial traction against the main strap portion 22. Then, as tension is increased the zone expands (propagates) through the rest of the tongue 30. The behavior of the crumpling of the tongue happens in place of crumpling of the underlying skin of the patient, thereby alleviating pinch. The increase in tension throughout the process can be clearly measured by comparing the indicia 38 along the strap portion 22 against the cut 42 or 40.

As will be appreciated by those skilled in the art, although the material used in fabrication of the tourniquet 20 is strong in tensile strength, acute angles of cut can introduce weak points which can tear when tension is applied. Thus, as a general guideline the diameter of the cuts in the tourniquet should be greater than 0.125 inch (3.2 mm). To that end, the cut 40 which is located at the interface of the base 32 and the tongue 30, is at least 0.125 inch (3.2 mm) in diameter to prevent premature tearing thereat. The cut 42 which is located at the intersection of the base 32 and the intermediate section 34 is also similarly constructed to help prevent tears. The cut 42 serves another distinct purpose by separating the base of the tourniquet from the locking zone 44. It is important to note that the greater the distance between the base 32 and locking zone 44 allows for more distinct motions between the act of tensioning the strap portion 22 and the act of locking the strap portion due to curvature of the limb (e.g., arm).

As mentioned above the tourniquet includes indicia 38 on its band to enable the user to determine the amount of tension applied by the tourniquet when it is tightened. This is accomplished by the user visually referring to those measuring lines 38 with reference to the cuts 40 and/or 42 or to the base 32.

The tourniquet may also include means to indicate the temperature of the ambient surroundings. That means may comprise temperature sensitive liquid crystals 108 (FIGS. 1A and 1E) located in an area on the tourniquet so as to be readily visible when the tourniquet is about to be placed, to verify that patient is not likely to be in a state of peripheral venous constriction to conserve heat.

In accordance with one preferred aspect of this invention the tourniquet may be provided in the form of a stack S of identical tourniquets 20, such as shown in FIG. 1B. The tourniquets of that stack are releasably secured to one another. Thus, when a pressure sensitive adhesive is used for the locking zone 44 as described above, the tourniquets include a release liner. The release liner can be provided in one of three locations, depending on how the tourniquets are provided. For example, if a plurality of tourniquets constructed like discussed above are provided in a series face down to form the stack like shown in FIG. 1B, a release liner patch 48 is located on the underside of each tourniquet so that it will cover the adhesive patch 44 on the upper side of the tourniquet located below it in the stack. Thus, the liner patch 48 on each tourniquet serves to releasably engage the adhesive of the locking zone of the underlying tourniquet, thereby releasably securing the tourniquets of the stack to one another so that the topmost tourniquet can be easily pulled from the stack for use.

As shown in FIGS. 1C and 1D tourniquets constructed in accordance with this invention may be folded to render them more compact for storage until they are ready for use. In particular, FIG. 1C shows the tourniquet 20, with its main strap portion 22 folded once lengthwise in order to hold the tourniquet in a compact state until ready for use. When the tourniquet is so arranged, another release liner patch 50 is used to protect the adhesive of the locking zone 44. In particular, the release liner patch 50 is located on the upper surface of the strap portion 22 adjacent its free end 24 so that when the strap is folded along a central fold line 52, such as shown in FIG. 1C, the release liner will be disposed over the adhesive making up the locking zone 44. The tourniquet 20 can be folded into an even smaller configuration (footprint) as shown in FIG. 1D, by folding its strap portion 22 along fold lines 54 and 56. In that case the tourniquet includes still another release liner patch 58, which is located on the upper surface of the strap portion 22 adjacent to the locking zone as shown in FIG. 1A for engaging the adhesive patch 44.

The use of the tourniquet 20 will now be described with reference to FIG. 1E. In particular, the tourniquet the tab 26 is grasped by the user between his/her thumb and forefinger and with the locking zone facing up. The main strap portion 22 is then loosely wrapped around the limb of the patient. With the opposing hand, the free end 24 of the strap portion 22 is guided though the opening 28 to form a loop. The band portion 22 is aligned to overlap itself, and the tongue 30, which is wider than band portion, so that the extension of tongue 30 on either side of the side edges of the band portion 22 is defined as a flange of tongue. The tourniquet is then adjusted approximately to the preferred position on the patient's limb, e.g., 1-3 cm proximal (caudal) to the venipuncture target, approximately centered in an axial plane. With the tourniquet in position the end of the tab 26 is held by one hand of the user. The band portion 22 is held by the user's other hand at any convenient point therealong, considering the diameter of the patient's limb on which the tourniquet is to be disposed. The grasped tab 26 and the grasped band portion are then pulled in opposite directions while approximately tangent to the curve of the patient's limb, so as not to prematurely intersect the adhesive patch 44 of the locking zone.

As should be appreciated by those skilled in the art at any time the tourniquet 20 may be temporarily positioned in approximate position with minimal tension, not impeding venous flow, while the user attends to patient needs, such as adjustments of blankets to improve body warmth to meet minimum indicated by an integral ambient temperature indicator, e.g., temperature sensitive liquid crystals, which are provided on the tourniquet as described earlier.

At this point in the process at least two options of usage are possible. In the first option: the tab 26 and band portion 22 are pulled until the adequate tension is reached. The user, by experience with the feel of the relatively inelastic band against pull on tab 26, learns the approximate additional tensioning required as indicated by the metered lines (the indicia 38) on the main strap of the tourniquet, advancing from lightly closed to fully tensioned. The amount of tension depends on multiple factors, including inherent tissue turgor, the diameter of the extremity, and the location of the tourniquet on the extremity. When the desired amount of tension is applied, the tourniquet is ready to be locked in place to maintain that tension. To that end, the user visually verifies that tension is maintained while he/she pulls the free end 24 of the band portion in toward parallel, to intersect the curve of the patient's limb at the location of the locking zone 44. The pressure of the underside of the band portion 22 on the adhesive of the locking zone 44 causes that adhesive to releasably secure the tourniquet in place about the limb of the patient with the desired degree of tightness since the adhesive is sufficiently strong in shear to hold such tension. In case any further adjustment of the tourniquet is desired, the free end 24 of the band portion 22 can be lifted off of the adhesive to unlock the tourniquet and the tourniquet readjusted as needed, e.g., the processes easily repeated.

In the second option of usage: the main strap is observed to be aligned with the axis of the tongue, with tongue flanges approximately symmetrically extending lateral, under the overlying strap portion 22. The user then holds the strap portion 22 close to loop exit, and temporarily presses with his/her thumb on base 32 just beyond base of tongue to gently anchor the closed loop.

It is anticipated that any user of the subject tourniquet will learn by experience to estimate the tissue turgor by the resistance to thumb pressure, and to detect deformity of tissue short of pinch. The user can note the position of the tourniquet using the indicia 38, so that by experience he/she learns the approximate additional tensioning required as indicated by that indicia. This tension depends on multiple factors, including inherent tissue turgor, the diameter of the extremity, and the location of the tourniquet on the limb. The user then continues to anchor the tourniquet in position on the patient's limb by pressing on the base 32 with his/her thumb and releasing his/her grasp on the tab 26 and shifting his/her thumb to a lateral flange of the tongue (the portions of the tongue which lie outside the edges of the overlying band portion 22). The user then gently depresses the flange to maintain anchor pressure. This enables additional pulling of the band with the user's now free hand along the tangent, remaining approximately aligned in axial plane. The user then adjusts the pull by sliding the band portion 22 in either direction along anchored tongue. The flange of the tongue 30 is then depressed as necessary to depress the underlying tissue and to straighten the tongue to minimize any potential to pinch the patient's skin at the tongue. When sufficient pressure is realized to increase tissue pressure to retard venous flow return, the user then angles the free end inward toward parallel to the curvature of patient's limb. The strap portion 22 is pressed down onto the locking zone 44 to lock the tourniquet in place at the set level of tightness. If any further adjustment is necessary the free end 24 can be lifted up to release the band section from the adhesive patch 44 of the locking zone and the processes easily repeated.

FIGS. 2A and 3 illustrate additional embodiments 20A and 20B of the tourniquet. Like the embodiment of FIGS. 1A-1E both of the embodiments 20A and 20B are cut from a single sheet of the same material as embodiment 20, and have similar main strap features. In the interest of brevity the common features that the tourniquets 20A and 20B share with the tourniquet 20 will be given the same reference numbers and a description of their construction, arrangement and operation will not be reiterated.

The tourniquet 20A is cut from a sheet of material into the shape shown in FIG. 2A. As can be seen the tourniquet 20A includes a tongue 60, which like the tongue 30 of the tourniquet 20 prevents pinching of the skin of the patient when the tourniquet is applied. Both of the embodiments 20A and 20B include main strap portions. In particular, the tourniquet 20A includes a main strap portion 62, while the tourniquet 20B includes a main strap portion 64. The main strap portions 62 and 64 of those tourniquets are shown concatenated and their measuring lines (indicia 38) are omitted in the interest of drawing simplicity. The critical difference in these embodiments is in their tabs. In particular, the tourniquet 20A includes a pair of symmetrical tabs 66 and 68, each including a hole 70 therein. Such an arrangement does not need any feed though during application. Both of the tabs 66 and 68 can be grabbed, with the thumb and forefinger of the user. The user is able to sense that that the tabs are held firmly by the sensation of his/her fingers against one another through the holes 70. FIG. 2B illustrates that when the tabs are grabbed they are face to face such that they project generally perpendicularly to the patient's limb's (e.g., arm's) axial plane.

The tourniquet of FIG. 3 also has a tongue 60 (constructed like the tongue 60 of the tourniquet 20A) to prevent pinch. The tourniquet 20B also includes a pair of tabs 72 and 74. The tabs 72 and 74 project outward from the sides of the tongue 60 in a similar manner to the tabs 66 and 68, but do not include holes therein. FIG. 3 illustrates the tabs 72 when folded over during fabrication, with the underside of tab 72 adhering to the topside of tab 74 by an interposed adhesive (not shown), and with both tabs lying generally parallel to the main strap 44. By combining the tabs 72 and 74 as just described a through hole 76 is formed in the tourniquet through which the free end of the main strap portion 64 can be extended (fed through). With the tabs 72 and 74 joined as just described a finger grip portion 78 results. The portion 78 includes finger grip lines or indicia 80, indicating that the portions of the conjoined tabs which are to be grabbed with the thumb and forefinger of the user to tighten the tourniquet about the arm of the patient.

The use and operation of the tourniquets of FIGS. 2 and 3 is nearly identical to that of the tourniquet of FIG. 1. One difference with the tourniquet 20A of FIG. 2 is that a single one of the tabs 66 and 68 can be grabbed and held in place against the patient's limb as tension is applied. FIG. 2B shows the tourniquet 20A in place ready to be tightened about the arm of the patient.

FIGS. 4A-4B illustrate still another exemplary embodiment of a tourniquet 20C constructed in accordance with the subject invention. The tourniquet 20C makes use of an alternative approach to prevent tissue pinching and to provide overall comfort and ensure consistent application. Like the other embodiments described above, the tourniquet 20C is cut from a single sheet of material into the shape shown in FIG. 4B. The tourniquet 20C is constructed in a manner somewhat like a conventional blood pressure cuff. To that end, as best seen in FIG. 4B the tourniquet basically comprises a band portion 82 in the form of an elongated web and a strip-like extension 84. The extension 84 is an elongated body which extends along the band portion and is connected to it by an intermediate portion 86. The extension is arranged to be folded (as will be described later) to form a pull strap (FIG. 4A) which extends out of a port 96 of the tourniquet. The pull strap 84 is arranged to be pulled by the user to tighten the tourniquet about the limb of the patient after the tourniquet is wrapped about that limb. To that end, the pull strap cooperates with plural slots in the band portion 82 to form an internal pulley arrangement. In particular, the band portion 82 includes a pair of transverse slots 88 which extend across a substantial portion of the width of the band portion 82 at the middle thereof.

The band portion is arranged to be folded along an inner transverse fold line 90 and a pair of outer transverse fold lines 92 located adjacent the slots so that the slots overlie each other to form a passageway through which the pull strap 84 may pass to form the pulley arrangement. To that end, the extension 84 is folded along its longitudinal axis to render it narrower. Then the folded extension is folded toward the band portion 82 along a fold line at the interface of the intermediate portion 86 and the band portion 82. A patch of adhesive 98A is located on the under surface (the surface opposite the surface shown in FIG. 4B) of the extension 84 adjacent the intermediate section 86 so that when the extension is folded to form the pull strap the adhesive patch 98A engages an opposed surface of the band portion 82 to form an anchor for the pull strap. The free end of the extension 84 is then passed through the slots 88 and out of a hole in the band portion. That hole forms the heretofore identified port 96. The port 96 preferably is in the form of a cleat lock. Once the free end of the pull strap has been extended through the cleat lock port, the two opposite ends of the band portion 82 are juxtaposed as shown in FIG. 4A so that they confront each other. As shown in FIG. 4A the inner surface of the band portion 82 (i.e., the surface on which the adhesive patch 98A is located) includes a plurality of lines of adhesive 98 along its periphery. Those adhesive lines secure the two confronting juxtaposed portions of the band portion 22 together and thus complete the tourniquet.

Like the other embodiments described heretofore the tourniquet 20C includes metering indicia 106 on it to provide an indication of the amount of tension applied. In particular, the metering indicia are located on the end portion of the pull strap 84 on the surface shown in FIG. 4B.

When the tourniquet is ready for use it can be readily formed into a sleeve or cuff to be wrapped about the limb of the patient. In order to hold the tourniquet in that configuration, the tourniquet includes releasably securable means in the form of a lock and cooperating locking zone. In the exemplary embodiment shown the lock preferably comprises a patch 100 of a pressure sensitive adhesive like used in the other embodiments 20, 20A and 20B. The locking zone (not shown), is on the undersurface of the tourniquet at the opposite end than the patch 100. Thus, when the tourniquet is wrapped in place about the limb of the patient the patch 100 on the free (outer) end of the tourniquet is disposed opposite the locking zone, and is pressed into place, thereby forming the tourniquet into a sleeve or cuff.

Tightening of the sleeve or cuff is achieved by the user placing his/her thumb and forefinger on top of the cleat lock at the outlet port 96 and holding it down. The free end of the pull strap 84 is then pulled tangentially from the cleat by the user's other hand while the cleat lock is held. The pulley arrangement provides mechanical advantage to increase the tension. This action causes a crumple zone portion 104 (FIG. 4B) of the band portion 82 to crumple, thereby shortening the length of the band portion so that the sleeve or cuff tightens around the patient's limb. The pulling of the pull strap out of the cuff causes the metering indicia 106 along the pull strap 84 to be revealed as the strap is pulled, thereby indicating the amount of tension applied. Once the necessary tension is reached the pull strap is pulled at an angle to engage the cleat lock and thereby releasably lock the tourniquet in place at the desired amount of tension. Alternatively, an optional pressure sensitive adhesive lock (not shown) can be provided on the top of the cuff adjacent the exit port. In such a case, after the pull strap is pulled to establish the desired amount of tension the pull strap is pressed parallel into engagement with the pressure sensitive adhesive lock to releasably lock the tourniquet in place at that level of tension.

It should be pointed out at this juncture that alternative means can be used to releasably secure the tourniquet about the limb of the patient. One such releasably securable means comprises VELCRO® multi-hook and multi-loop fasteners.

As will be appreciated by those skilled in the art, when the tourniquet 20C is in place on the limb of the patient the sleeve or cuff encloses the pull strap 84 preventing it from coming in direct contact with the patient's limb, and allowing the pull strap to move freely across the inside of the cuff through the slots 86 and 88 and out of the port 96.

Turning now to FIG. 5, yet another exemplary preferred embodiment of the tourniquet 20D is shown and will now be described. The tourniquet 20D is a variant of the tourniquet 20B shown in FIG. 3. Thus, the features of tourniquet 20D that are common to tourniquet 20B will be given the same reference numbers and the details of their construction and operation will not be reiterated in the interest of brevity. As can be seen the tourniquet 20D includes a variant tab 110 which provides feedback to the user showing the amount of tension applied by the tourniquet when it is tightened. The tab 110 basically comprises a body of a relatively rigid plastic having a base portion 112, and an upper portion 114. The base portion 112 is fixedly secured to a portion of the band portion 64 below the tongue 60. The upper portion of the tab is not secured to the tongue and includes a finger grip zone 116 at the upper end of the tab and a central portion 118 located between the finger grip zone and the base portion. A slot 120 is located in the central portion immediately above the base portion 112. The central portion is arranged to stretch upon the application of tension to the tab. To that end, it includes a pair of flex legs 122 that bridge the central portion of the tab from the finger grip zone to the base portion. The legs 122 are relatively thin so that they can flex when tension is applied to the tab (as will be described shortly), whereupon the central portion of the tab stretches. A tension indicator, in the form of a finger 124, projects downward from the finger grip zone between a pair of fingers 126 that project upward from the base portion. The fingers 126 include indicia along their length, which in cooperation with the free end of the finger 124 serve to provide an indication of the amount of tension applied by the tourniquet 20D when it is tightened.

In use the free end portion of the tourniquet is wrapped around the limb of the patient and brought over the upper surface of the tongue 60, under the upper and intermediate portions of the tab 110 and out of the slot 120. In order to tighten the tourniquet the user grasps the finger grip zone 116 of the tab between his/her thumb and forefinger of one hand while the pulling the free end 24 of the band 64 away from the slot 120. This action applies a force to the leading edge of the slot, whereupon the tab 110 begins to stretch at its central portion 118, i.e., its legs 122 flex and deform, so that the tip of the indicating finger 124 moves to a new position with respect to the indicia on the fingers 126, thereby indicating the amount of tension applied. The user can apply as much tension as desired. Once that level of tension is achieved (which is indicated by the indicating finger and the associated indicia), the free end 24 of the band 64 can be brought into engagement with the adhesive patch 44 on the band to releasably lock the tourniquet in place.

It should be noted that other stretchable arrangements are contemplated for the tab, e.g., other shaped flex legs can be used, the slot can have a side opening so that the free end of the band 22 can be inserted into it from a lateral direction, etc. Furthermore, other tension indicators can be used. For example, it is contemplated that the band 64 include a plurality of accordion-like pleats, with respective patches of adhesive interposed between immediately adjacent pleats, and with each succeeding patch of adhesive being of greater tensile strength than the preceding patch. Thus, the amount of tension applied will be indicated by the number of pleats that have opened when tension has been applied to the band sufficient to overcome the tensile strength of the patch(es) between the accordion pleats.

As should be appreciated from the foregoing the subject invention exhibits numerous advantages over the prior art. In particular, it provides tourniquets including means to prevent pinching and pulling of hair along the extremity. It provides a form which prevents the body of the tourniquet from narrowing and has means to indicate to the user a useful sense of tensioning. In addition, its construction enables the use of more controlled force in tensioning the tourniquet and makes use of securing means which produce no scrap material during application and which are conducive to accurate tensioning, rapid application, or adjustment. All of those advantages are accomplished by a device whose construction is cost effective and suitable for economic disposal.

Without further elaboration the foregoing will so fully illustrate our invention that others may, by applying current or future knowledge, adopt the same for use under various conditions of service.

We claim:

1. A disposable tourniquet formed of a thin flexible, non-stretchable material configured to be wrapped about a limb of a patient and tightened to reduce circulation and for controlling the amount of tension applied, said tourniquet comprising a main band portion having a pair of ends, one of said ends being in the form of a tab, said tab comprising a passageway, a tongue portion, and a crumple zone, said passageway comprising a through hole in which said tongue portion is located, with said crumple zone connecting said tongue portion to said main band portion, the other of said ends of said main band portion being a free end, said tourniquet being configured for enabling said main band portion to be wrapped around the limb of the patient and tightened, with said free end extended through said through hole, whereupon a portion of said main band portion adjacent said free end extends over said tongue portion and slides with respect thereto and wherein said tongue flanks said main band portion, and with said crumple zone being configured to crumple upon the application of excess tension to said main band portion to prevent over-tensioning.

2. The disposable tourniquet of claim 1 wherein said tourniquet comprises releasable securable means to enable the re-positionable securing and releasing of said tourniquet.

3. The disposable tourniquet of claim 2 wherein said releasably securable means comprises a pressure sensitive adhesive.

4. The disposable tourniquet of claim 3 additionally comprising a release liner arranged to be disposed over said pressure sensitive adhesive.

5. The disposable tourniquet of claim 1 wherein said tourniquet is provided as a group of plural tourniquets releasably secured to one another.

6. The group of disposable tourniquets of claim 5 wherein said group comprises a stack of plural tourniquets.

7. The group of disposable tourniquets of claim 6 wherein said stack of plural tourniquets are releasably secured together by a pressure sensitive adhesive and wherein each of said tourniquets includes a release liner for engagement with the pressure sensitive adhesive of the immediately adjacent tourniquet in said stack.

8. The disposable tourniquet of claim 1 wherein said tourniquet is configured to be folded into a compact configuration and held in such configuration until ready for use.

9. The disposable tourniquet of claim 8 wherein said tourniquet comprises a pressure sensitive adhesive and wherein a portion of said tourniquet is arranged to be brought into engagement with said pressure sensitive adhesive to hold said tourniquet in said compact configuration.

10. The disposable tourniquet of claim 9 additionally comprising a release liner located on said tourniquet for engagement with said pressure sensitive adhesive to hold said tourniquet in said compact configuration.

11. The disposable tourniquet of claim 1 wherein said tourniquet is configured so that it prevents pinching of the skin and pulling of the hair of the limb.

12. The disposable tourniquet of claim 1 wherein said tourniquet is configured such that when tightened about the limb of the patient it increases tissue pressure to produce venous distention with minimum tissue torsion, and traction to the skin and hair of the patient.

13. The disposable tourniquet of claim 1 additionally comprising means for indicating the amount of tension applied.

14. The disposable tourniquet of claim 13 wherein said means for indicating the amount of tension applied comprises indicia appearing on said tourniquet.

15. The disposable tourniquet of claim 1 additionally comprising means for indicating temperature near the skin of the patient at the limb and ambient temperature.

16. The disposable tourniquet of claim 15 wherein said means for indicating ambient temperature comprises liquid crystals.

17. A method of applying a tourniquet around a patient's limb to reduce circulation, said tourniquet being formed of a thin flexible, non-stretchable material and comprising a main band portion having a pair of ends, one of said ends being in the form of a tab, said tab comprising a passageway, a tongue portion, and a crumple zone, said passageway comprising a through hole in which said tongue portion is located, with said crumple zone connecting said tongue portion to said main band portion, the other of said ends of said main band portion being a free end, said method comprising:

wrapping said band around the limb of the patient with said free end extended through said through hole, whereupon a portion of said main band portion adjacent said free end extends over said tongue portion and slides with respect thereto while said tongue flanks said main band portion and with said crumple zone crumpling upon the application of excess tension to said main band so that a desired amount of tension is applied; and locking said band in place when said desired amount of tension is achieved, whereupon said tourniquet increases tissue pressure on the patient's limb to produce venous distention with minimum tissue torsion, and traction to the skin and hair of the patient.

18. The method of claim 17 wherein the tourniquet includes an outer surface, an inner surface and a pressure sensitive adhesive located on said outer surface, and wherein said method comprises bringing a portion of said inner surface of said tourniquet into engagement with said pressure sensitive adhesive to lock said band in place.

19. The method of claim 17 wherein said band additionally comprises indicia on said band, and wherein said method additionally comprises utilizing said indicia to determine the amount of tension applied by said tourniquet.

20. The method of claim 17 wherein said band additionally comprises means on said tourniquet to indicate the ambient temperature near the skin of the patient underlying said tourniquet.

* * * * *